US011806134B2

(12) United States Patent
Prais et al.

(10) Patent No.: US 11,806,134 B2
(45) Date of Patent: Nov. 7, 2023

(54) SENSOR ASSEMBLY APPARATUS AND METHODS FOR CONTINUOUS GLUCOSE MONITORS

(71) Applicant: Ascensia Diabetes Care Holdings AG, Basel (CH)

(72) Inventors: Eugene Prais, West Milford, NJ (US); Jennifer L. Gass, Tarrytown, NY (US); Nihir Patel, Stamford, CT (US); Nikhil M. Shah, Edison, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 129 days.

(21) Appl. No.: 15/974,680

(22) Filed: May 8, 2018

(65) Prior Publication Data

US 2018/0325433 A1 Nov. 15, 2018

Related U.S. Application Data

(60) Provisional application No. 62/657,612, filed on Apr. 13, 2018, provisional application No. 62/503,859, filed on May 9, 2017.

(51) Int. Cl.
*A61B 5/145* (2006.01)
*A61B 5/00* (2006.01)
*A61B 5/1486* (2006.01)

(52) U.S. Cl.
CPC ...... *A61B 5/14532* (2013.01); *A61B 5/14503* (2013.01); *A61B 5/6848* (2013.01);
(Continued)

(58) Field of Classification Search
CPC ............ A61B 5/14532; A61B 5/14503; A61B 5/14546; A61B 5/1411; A61B 5/150022;
(Continued)

(56) References Cited

U.S. PATENT DOCUMENTS 8,224,414 B2   7/2012  Kellogg et al.
8,333,714 B2  12/2012  Stafford
(Continued)

FOREIGN PATENT DOCUMENTS

CN   101268932 A   9/2008
CN   100591265 C   2/2010
(Continued)

OTHER PUBLICATIONS

International Search Report and Written Opinion of International Application No. PCT/EP2018/061820 dated Aug. 17, 2018.
(Continued)

*Primary Examiner* — Carrie R Dorna
*Assistant Examiner* — Karen E Toth
(74) *Attorney, Agent, or Firm* — Erise IP, P.A.

(57) ABSTRACT

In some embodiments, a sensor assembly for a continuous glucose monitoring system is provided that includes (1) a sensor carrier having a sensor unit receiving area and an electronics receiving area, the electronics receiving area including a substrate; (2) a sensor unit having a sterilized region, the sterilized region including at least a portion of a sensor and an introducer; and (3) electronics for the continuous glucose monitoring system. The sensor unit is positioned within the sensor unit receiving area of the sensor carrier and the electronics are positioned on the substrate within the electronics receiving area of the sensor carrier so as to form a sensor assembly having the sensor electrically connected to the substrate of the electronics receiving area while maintaining sterilization of the sterilized region of the sensor unit. Numerous other aspects are provided.

20 Claims, 11 Drawing Sheets

(52) U.S. Cl.
CPC ........ *A61B 5/6849* (2013.01); *A61B 5/14865* (2013.01); *A61B 2560/045* (2013.01); *A61B 2560/0443* (2013.01); *A61B 2562/12* (2013.01)

(58) Field of Classification Search
CPC ..... A61B 5/145; A61B 5/1451; A61B 5/1459; A61B 5/1486; A61B 5/14865
See application file for complete search history.

(56) References Cited

U.S. PATENT DOCUMENTS

| | | | |
|---|---|---|---|
| 8,862,198 | B2 | 10/2014 | Stafford |
| 9,119,578 | B2 | 9/2015 | Haghgooie et al. |
| 9,662,071 | B2 | 5/2017 | Ohkoshi |
| 9,980,670 | B2 | 5/2018 | Funderburk et al. |
| 10,292,632 | B2 | 5/2019 | Lee et al. |
| 2008/0027296 | A1* | 1/2008 | Hadvary ............ A61B 5/14532 600/309 |
| 2008/0097246 | A1 | 4/2008 | Stafford et al. |
| 2008/0255440 | A1 | 10/2008 | Eilersen et al. |
| 2008/0319414 | A1 | 12/2008 | Yodfat et al. |
| 2009/0257911 | A1* | 10/2009 | Thomas ................ A61L 2/087 422/22 |
| 2010/0198033 | A1 | 8/2010 | Krulevitch et al. |
| 2011/0106126 | A1 | 5/2011 | Love et al. |
| 2012/0157801 | A1* | 6/2012 | Hoss ................ A61B 5/14503 600/309 |
| 2012/0197098 | A1 | 8/2012 | Donnay et al. |
| 2013/0150691 | A1* | 6/2013 | Pace .................... A61B 5/1451 600/347 |
| 2013/0267811 | A1 | 10/2013 | Pryor et al. |
| 2014/0066730 | A1* | 3/2014 | Roesicke ............ A61B 5/1459 600/309 |
| 2015/0018639 | A1* | 1/2015 | Stafford ............. A61B 5/14546 600/309 |
| 2016/0058344 | A1 | 3/2016 | Peterson et al. |
| 2016/0058474 | A1 | 3/2016 | Peterson et al. |
| 2016/0331284 | A1* | 11/2016 | Pace ................. A61B 5/14503 |
| 2017/0143243 | A1* | 5/2017 | Deck ...................... A61B 50/30 |
| 2017/0188912 | A1* | 7/2017 | Halac ................... A61B 5/6848 |
| 2017/0202488 | A1 | 7/2017 | Stafford |
| 2017/0245798 | A1 | 8/2017 | Ohkoshi |
| 2018/0116570 | A1 | 5/2018 | Simpson et al. |
| 2018/0116572 | A1 | 5/2018 | Simpson et al. |
| 2020/0009745 | A1 | 1/2020 | Grossard et al. |
| 2020/0100713 | A1 | 4/2020 | Simpson et al. |
| 2020/0214633 | A1 | 7/2020 | Antonio et al. |
| 2022/0071528 | A1 | 3/2022 | Avirovikj et al. |

FOREIGN PATENT DOCUMENTS

| | | | | |
|---|---|---|---|---|
| CN | 102065908 | A | 5/2011 | |
| CN | 103826528 | A | 5/2014 | |
| EP | 2636372 | A1 | 9/2013 | |
| EP | 3170453 | A1 | 5/2017 | |
| EP | 3449827 | A1 | 3/2019 | |
| JP | 2008508971 | A | 3/2008 | |
| JP | 2008508971 | A | 3/2008 | |
| JP | 2008246204 | A | 10/2008 | |
| JP | 2008246204 | A | 10/2008 | |
| JP | 2015509011 | A | 3/2015 | |
| JP | 2015509011 | A | 3/2015 | |
| TW | 201340940 | A | 10/2013 | |
| WO | WO2013090215 | A2 | 6/2013 | |
| WO | WO-2016036924 | A2 | 3/2016 | |
| WO | WO2018027940 | A1 | 2/2018 | |
| WO | WO2018195286 | A1 | 10/2018 | |
| WO | WO-2018206552 | A1 * | 11/2018 | ......... A61B 5/14532 |
| WO | WO2019054113 | A1 | 3/2019 | |
| WO | WO2019176324 | A1 | 9/2019 | |

OTHER PUBLICATIONS

IPRP of International Application No. PCT/EP2018/061820 mailed Nov. 21, 2019.
Japanese Patent Application No. 2019-561889, Notice of Allowance, dated Sep. 20, 2022.
U.S. Appl. No. 17/581,842, filed Jan. 21, 2022, Avirovikj et al.
U.S. Appl. No. 17/581,844, filed Jan. 21, 2022, Avirovikj et al.
Taiwan Patent Application No. 107115665, Official Letter and Search Report, dated Dec. 8, 2022.
China Patent Application No. 201880030828.8, Decision on Rejection, dated Feb. 2, 2023.
European Patent Application 18725436.2 Office Action dated Aug. 3, 2023.

* cited by examiner

SENSOR ASSEMBLY APPARATUS AND METHODS FOR CONTINUOUS GLUCOSE MONITORS

The present application claims priority to and the benefit of U.S. Provisional patent application Ser. No. 62/503,859, filed May 9, 2017 and titled "SYSTEMS, APPARATUS AND METHODS FOR CONTINUOUS GLUCOSE MONITOR SENSOR INSERTION" and U.S. Provisional Patent Application No. 62/657,612, filed Apr. 13, 2018, and titled "SENSOR ASSEMBLY APPARATUS AND METHODS FOR CONTINUOUS GLUCOSE MONITORS," each of which is hereby incorporated by reference herein in its entirety for all purposes.

FIELD

The present disclosure relates generally to continuous glucose monitoring (CGM) and more particularly to apparatus and methods for sensor assemblies for CGMs.

BACKGROUND

Existing CGM products provide frequent measurements of a patient's glucose levels without the need for each such measurement to be accompanied by the drawing of blood, such as by "finger sticks." CGM products may include a sensor portion that is inserted so as to be located under the skin, and a processing portion that is adhered to the outer surface of the skin, for example the abdomen or back of the upper arm. These CGM products are worn for a number of days before being removed and replaced.

The sensor that has been inserted under the skin provides a signal to the processing portion of the CGM product, and that signal is indicative of the patient's blood glucose level. These measurements may be made automatically many times throughout the day (e.g., every 5 minutes or at some other interval).

The processing portion of a CGM product may include electrical circuitry for interpreting the signal provided by the sensor, and for storing and/or communicating information regarding the patient's blood glucose levels.

SUMMARY

In some embodiments, a sensor assembly for a continuous glucose monitoring system is provided that includes (1) a sensor carrier having a sensor unit receiving area and an electronics receiving area, the electronics receiving area including a substrate; (2) a sensor unit having a sterilized region, the sterilized region including at least a portion of a sensor and an introducer; and (3) electronics for the continuous glucose monitoring system. The sensor unit is positioned within the sensor unit receiving area of the sensor carrier and the electronics are positioned on the substrate within the electronics receiving area of the sensor carrier so as to form a sensor assembly having the sensor electrically connected to the substrate of the electronics receiving area while maintaining sterilization of the sterilized region of the sensor unit.

In some embodiments, an insertion device for a continuous glucose monitoring system is provided that includes (1) an insertion unit; (2) a sensor carrier positioned within the insertion unit and having a sensor unit receiving area and an electronics receiving area, the electronics receiving area including a substrate; (3) a sensor unit having a sterilized region, the sterilized region including at least a portion of a sensor and an introducer; and (4) electronics for the continuous glucose monitoring system. The sensor unit is positioned within the sensor unit receiving area of the sensor carrier and the electronics are positioned on the substrate within the electronics receiving area of the sensor carrier so as to form a sensor assembly having the sensor electrically connected to the substrate of the electronics receiving area while maintaining sterilization of the sterilized region of the sensor unit. The insertion device also includes a removable cover attached to the insertion unit that interfaces with the sensor unit such that removal of the removable cover exposes the introducer and the sensor.

In some embodiments, a sterilized sensor unit for a continuous glucose monitor is provided that includes (1) a sensor, an introducer having an insertion shaft, and an insertion shaft cover; and (2) a sensor housing having (a) a first end configured to receive the insertion shaft of the introducer; (b) a second end having a sealing surface configured to seal against the insertion shaft cover; and (c) an insertion shaft opening that extends between the first end and the second end and having a width that allows the insertion shaft of the introducer to travel through the opening. A portion of the sensor and insertion shaft of the introducer are positioned within the insertion shaft opening of the sensor housing. The insertion shaft cover is sealingly coupled to the second end of the sensor housing, the insertion shaft cover having an inner region. The sensor housing, the introducer and the insertion shaft cover form a sealed region that includes the inner region of the insertion shaft cover. The sealed region and all components within the sealed region are sterilized.

In some embodiments, a method of forming a sensor assembly for a continuous glucose monitoring system includes (1) providing a sensor carrier having a sensor unit receiving area and an electronics receiving area, the electronics receiving area including a substrate; (2) providing a sensor unit having a sterilized region, the sterilized region including at least a portion of a sensor and an introducer; (3) providing electronics for the continuous glucose monitoring system; and (4) positioning the sensor unit within the sensor unit receiving area of the sensor carrier and positioning the electronics on the substrate within the electronics receiving area of the sensor carrier so as to form a sensor assembly having the sensor electrically connected to the substrate of the electronics receiving area while maintaining sterilization of the sterilized region of the sensor unit.

In some embodiments, a method of forming an insertion device for a continuous glucose monitoring system includes (1) providing a sensor carrier having a sensor unit receiving area and an electronics receiving area, the electronics receiving area including a substrate; (2) providing a sensor unit having a sterilized region, the sterilized region including at least a portion of a sensor and an introducer; (3) providing electronics for the continuous glucose monitoring system; (4) positioning the sensor unit within the sensor unit receiving area of the sensor carrier and positioning the electronics on the substrate within the electronics receiving area of the sensor carrier so as to form a sensor assembly having the sensor electrically connected to the substrate of the electronics receiving area while maintaining sterilization of the sterilized region of the sensor unit; (5) providing an insertion unit; (6) positioning the sensor carrier within the insertion unit; and (7) attaching a removable cover to the insertion unit that interfaces with the sensor unit such that removal of the removable cover exposes the introducer and the sensor.

In some embodiments, a method of forming a sterilized sensor unit for a continuous glucose monitor includes (1)

providing a sensor, an introducer having an insertion shaft, and an insertion shaft cover; and (2) providing a sensor housing having (a) a first end configured to receive the insertion shaft of the introducer; (b) a second end having a sealing surface configured to seal against the insertion shaft cover; and (c) an insertion shaft opening that extends between the first end and the second end and having a width that allows the insertion shaft of the introducer to travel through the opening, a portion of the sensor and insertion shaft of the introducer positioned within the insertion shaft opening of the sensor unit. The method further includes (3) sealingly coupling the insertion shaft cover to the second end of the sensor housing, the insertion shaft cover having an inner region; (4) inserting the introducer into the first end so that the sensor housing, the introducer and the insertion shaft cover form a sealed region that includes the inner region of the insertion shaft cover; and (5) sterilizing the sealed region and all components within the sealed region.

Other features, aspects, and advantages of embodiments in accordance with the present disclosure will become more fully apparent from the following detailed description, the subjoined claims, and the accompanying drawings by illustrating a number of example embodiments and implementations. Various embodiments in accordance with the present disclosure may also be capable of other and different applications, and its several details may be modified in various respects, all without departing from the spirit and scope of the claims. Accordingly, the drawings and descriptions are to be regarded as illustrative in nature, and not as restrictive. The drawings are not necessarily drawn to scale.

DETAILED DESCRIPTION

Embodiments of the present invention allow formation of a sensor unit having a sensor and an insertion shaft of an introducer that may be separately sterilized and then easily and securely connected to an electronic circuit of a continuous glucose monitor during assembly. The sensor unit may be sterilized using a process such as electron or gamma beam sterilization which may be effective for sterilizing sensors and insertion shafts without damaging the enzymes used by the sensors for glucose detection, but which may damage sensitive electrical circuitry of the continuous glucose monitor.

In some embodiments, the sensor unit may include a sealed, sterilized region formed by a sensor housing, an introducer and a cover of the insertion shaft of the introducer. The sensor unit may form part of a sensor assembly that includes a sensor carrier which joins the sensor unit to electronics for a continuous glucose monitor, while maintaining sterilization of the sensor and insertion shaft of the introducer. In some embodiments, the sensor assembly may be employed within an insertion device which removes the cover of the insertion shaft to expose the sensor and insertion shaft when a cover of the insertion device is removed (e.g., prior to insertion).

In order to perform continuous glucose monitoring, a sensor is inserted into a patient and electrical circuitry is coupled to the sensor. The electrical circuitry may be used for processing information obtained from the sensor, and transmitting information to one or more external devices used by patients and/or healthcare providers to, among other things, track the patient's blood glucose level over time. A housing containing the electrical circuity is adhered to the patient's skin with the sensor extending into the patient, and remains on the patient's skin for several days (e.g., up to a week or more in some cases).

Embodiments provided herein may simplify manufacturing of continuous glucose monitoring devices by providing a sensor unit that may be separately sterilized and then easily and securely connected to an electronic circuit of a continuous glucose monitor during assembly. Embodiments provided herein may also simplify the insertion process for patients. For example, use of an insertion device which exposes the sensor and insertion shaft prior to insertion when a cover of the insertion device is removed may reduce the number of steps a patient must perform during insertion.

These and other embodiments of the present disclosure are described below with reference to FIGS. 1A-7.

Figure 1A:
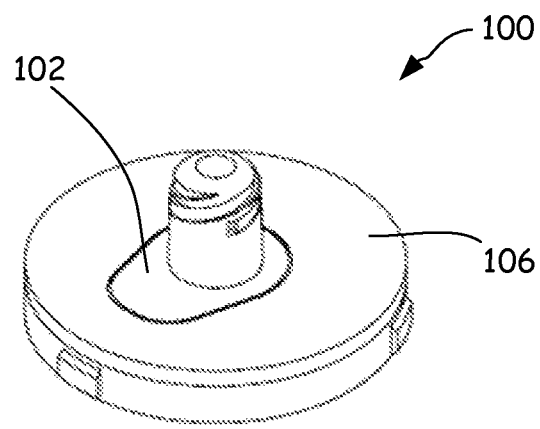
FIGS. 1A and 1B are a side-perspective view and an exploded, side-perspective view, respectively, of a sensor assembly provided in accordance with one or more embodiments.
Figure 1B:
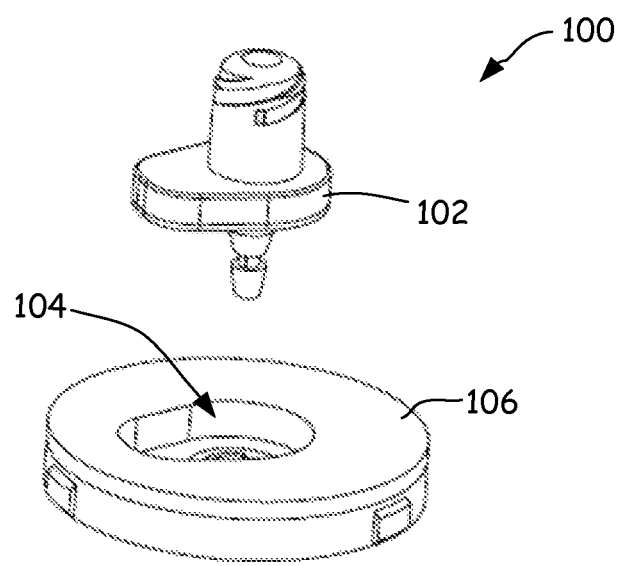

FIGS. 1A and 1B are a side-perspective view and an exploded, side-perspective view, respectively, of a sensor assembly 100 provided in accordance with one or more embodiments. With reference to FIGS. 1A and 1B, sensor assembly 100 includes a sensor unit 102 which fits within a sensor unit receiving area 104 of a sensor carrier 106. As will be described below, sensor unit 102 includes a sensor and insertion shaft in a sterilized region of the sensor unit 102, and couples to electronic circuitry within sensor carrier 106 when positioned within sensor unit receiving area 104 of sensor carrier 106.

Figures 2A, 2B:
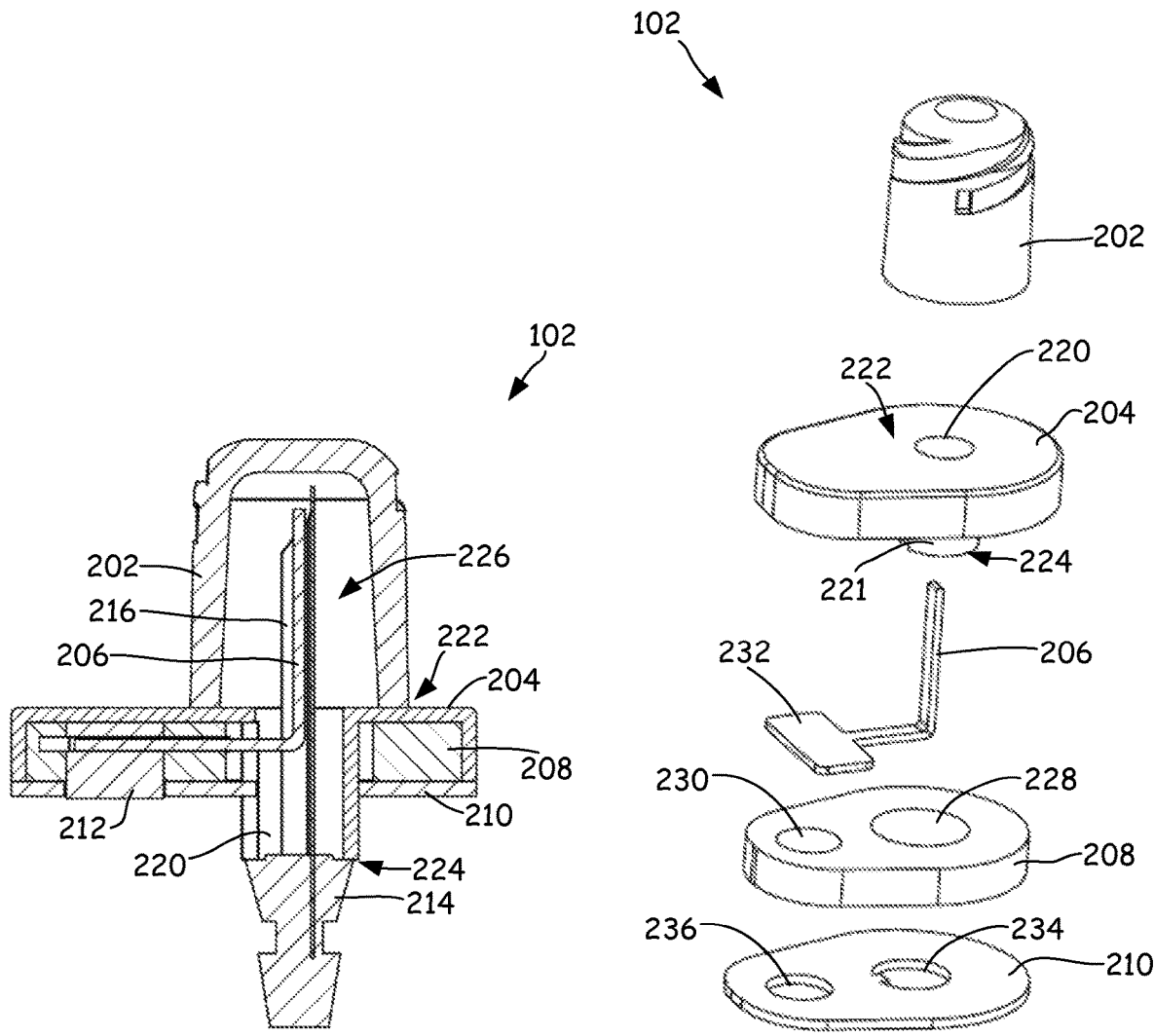
FIGS. 2A and 2B are a side cross-sectional view and an exploded, side-perspective view, respectively, of a sensor unit provided in accordance with one or more embodiments.

FIGS. 2A and 2B are a side cross-sectional view and an exploded, side-perspective view, respectively, of sensor unit 102 provided in accordance with one or more embodiments. With reference to FIGS. 2A and 2B, sensor unit 102 includes an insertion shaft cover 202, a top member 204, a sensor 206, a spacer pad 208, a bottom member 210, a conductive member 212, and an introducer 214 having an insertion shaft 216 and handle 218.

Insertion shaft cover 202 covers sensor 206 and insertion shaft 216, and in some embodiments, is sealed against top member 204. For example, insertion shaft cover 202 may be sealed relative to top member 204 using an O-ring, a sealant such as silicone, or the like. Top member 204 includes an insertion shaft opening 220, defined by cylindrical member 221, that extends between a first end 222 (e.g., a top surface of top member 204) and a second end 224, and has a width that allows insertion shaft 216 to travel through the insertion shaft opening 220.

As shown in FIG. 2A, a portion of sensor 206 and insertion shaft 216 are positioned within insertion shaft opening 220. In some embodiments, handle 218 of introducer 214 may seal against the second end 224 of insertion shaft opening 220 (e.g., using an O-ring, a sealant such as silicone, or the like). In this manner, insertion shaft cover 202, insertion shaft opening 220 and introducer 214 may form a sealed region 226 that houses a portion of sensor 206 and a portion of insertion shaft 216 that may extend within a patient during insertion. As described further below, sealed region 226 and all components within sealed region 226, such as sensor 206 and insertion shaft 216, may be sterilized (e.g., using an electron beam, a gamma beam, or the like).

Spacer pad 208 is configured to hold sensor 206 in position within sensor unit 102. For example, spacer pad 208 extends the height and width of the internal space defined by top member 204 and bottom member 210, and surrounds sensor 206 as sensor 206 extends into the internal space defined by top member 204 and bottom member 210. In some embodiments, spacer pad 208 may be a polymer, rubber or other elastomer member and/or may be slightly compressed when positioned within sensor unit 102 between top member 204 and bottom member 210.

Space pad 208 includes a first opening 228 through which cylindrical member 221 of top member 204 may extend, and a second opening 230 through which conductive member 212 may extend. Conductive member 212 may be a conductive elastomer pad, for example, that makes electrical contact to a contact portion 232 of sensor 206 and allows sensor 206 to make electrical contact with a substrate that supports electronic circuitry of a continuous glucose monitor as described further below.

Bottom member 210 attaches to top member 204. For example top member 204 may be glued or otherwise attached to bottom member 210, defining an inner space for sensor 206, spacer pad 208 and conductive member 212 as shown. Bottom member 210 includes a first opening 234 through which cylindrical member 221 of top member 204 may extend, and a second opening 236 through which conductive member 212 may extend.

In some embodiments, insertion shaft cover 202, top member 204, bottom member 210, and/or handle 218 of introducer 214 may be made from acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), low-density polyethelene (LDPE) or a similar material. Other materials may be used.

In some embodiments, sensor 206 may be made from one or more sheets, including a substrate layer such as a vinyl polymer with subsequent layers of gold, silver chloride, and/or various coatings and enzymes suitable for the sensor's use in determining blood glucose levels. Other sensor materials may be used.

In some embodiments, insertion shaft 216 may be a hollow cylinder with a sharply pointed end used to introduce a sensor into a patient's interstitial fluid. Insertion shaft 216 may be used to insert sensor 206 into a patient such that sensor 206, or at least a portion of sensor 206, is located under the patient's skin.

In some embodiments, insertion shaft 216 of introducer 214 may be made from a metal such as stainless steel or from another material such as plastic. In some embodiments, insertion shaft 216 is insert-molded with a plastic handle 218, and insertion shaft 216 may be, but is not limited to, a round C-channel tube, a round U-channel tube, a stamped sheet metal part folded into a square U-profile, a molded/cast metal part with a square U-channel profile, or a solid metal cylinder with an etched or ground square U-channel. In some example embodiments, for insertion shaft 216 implemented as a C-channel or U-channel tube insertion shaft, the tube may have an inner diameter in the range of 400 µm to 700 µm and a thickness in the range of 100 µm to 250 µm. In some example embodiments, for insertion shaft 216 implemented as stamped sheet metal folded into a square U-profile, the inner width and height may be in a range from 400 µm to 700 µm, with a wall thickness in a range from 100 µm to 250 µm. In some example embodiments, for insertion shaft 216 implemented as a molded or cast metal part, the outer diameter of insertion shaft 216 may be in the range of 1200 µm to 2000 µm, and inner channel of insertion shaft 216 may have a width and height between 400 µm to 700 µm. In some example embodiments, the length of introducer 214 including handle 218 and insertion shaft 216 may be approximately 18 to 22 mm, and the length of insertion shaft 216 of introducer 214 may be about be approximately 12 mm to 15 mm. Other introducer and/or insertion shaft configurations, sizes and/or materials may be used.

As mentioned, sensor unit 102 includes sealed region 226 in which a portion of sensor 206 and insertion shaft 216 are housed. Following assembly of sensor unit 102, sealed region 226, and sensor 206 and insertion shaft 216 residing therein, may be sterilized. Example sterilization methods include electron beam sterilization, gamma beam sterilization or any other suitable sterilization method.

Figure 3A:
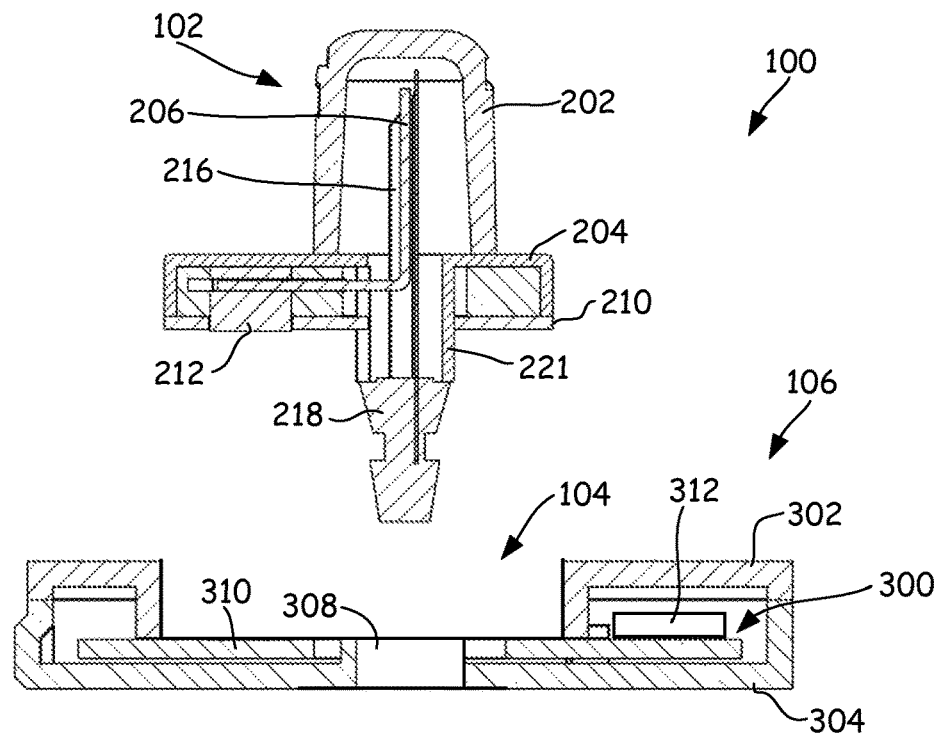
FIG. 3A is an exploded cross-sectional view and FIG. 3B is a cross-sectional view, respectively, of a sensor assembly in accordance with an example embodiment of the disclosure.
Figure 3B:
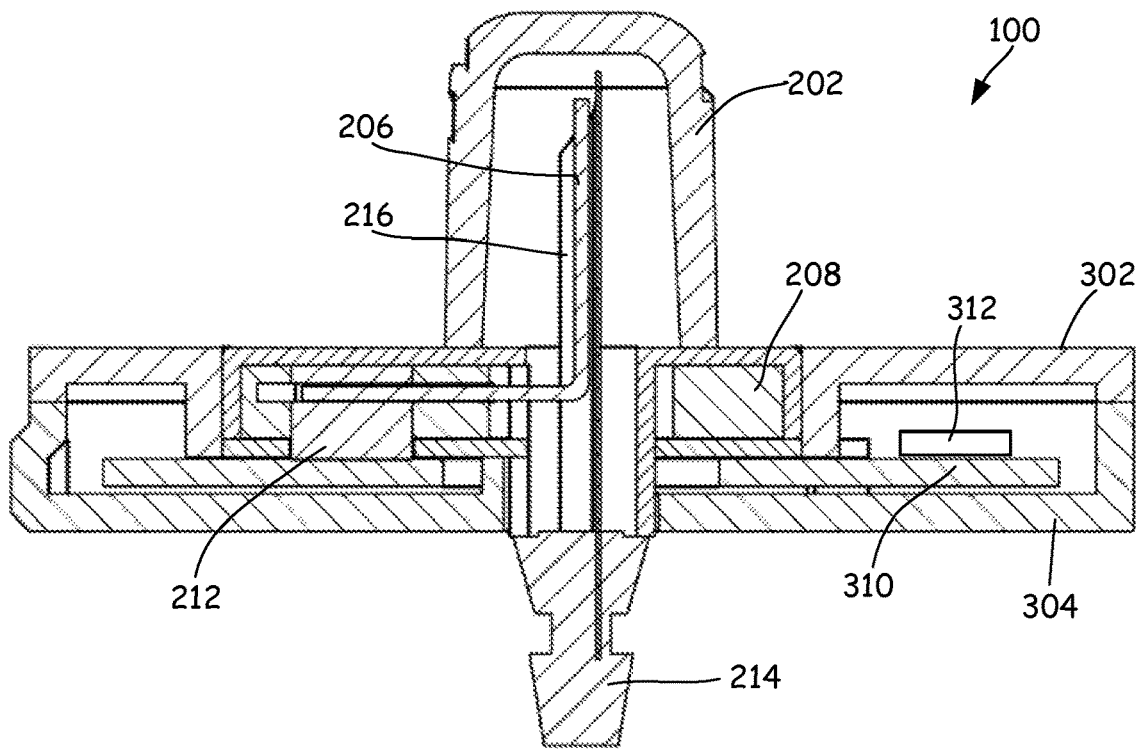

FIG. 3A is an exploded cross-sectional view and FIG. 3B is a cross-sectional view, respectively, of a sensor assembly 100 in accordance with an example embodiment of the disclosure. With reference to FIGS. 3A-3B, sensor assembly 100 includes sensor carrier 106 having sensor unit receiving area 104 and an electronics receiving area 300 formed therein. Sensor carrier 106 includes a top carrier member 302 coupled to a bottom carrier member 304 which couple to define the electronics receiving area 300. In some embodiments, top carrier member 302 and/or bottom carrier member 304 may be formed from the same material used to form top member 204 and bottom member 210 of sensor unit 102, although other materials may be used. Bottom carrier member 304 includes an opening 308 through which cylindrical member 221 of sensor unit 102 may pass when sensor unit 102 is positioned within sensor unit receiving area 104 of sensor carrier 106.

Sensor assembly 100 includes a substrate 310 positioned within electronics receiving area 300. In one or more embodiments, substrate 310 may be, for example, a 4-layer printed circuit board, a laminated circuit board, a flex circuit, a flex printed circuit board, or any other suitable substrate for positioning and/or interconnecting electronic circuitry (e.g., one or more insulating or dielectric materials with electrical conductors for connecting circuitry). Substrate 310 may be electrically non-conductive, and may have electrically conductive traces formed thereon and therein, for example. In some example embodiments, substrate 310 may have a thickness in a range of, but not limited to, about 0.6 mm to 0.8 mm. Other substrate and/or printed circuit board configurations, sizes and/or materials may be employed.

Substrate 310 may have electrical circuitry 312 disposed on, and/or in, substrate 310. Electrical circuitry 312 may include circuits housed in packages that are mounted directly to substrate 310, and/or coupled to corresponding sockets, which are attached to substrate 310. Example electrical circuitry 312 may include one or more processors, memory, a battery, a transmitter and/or receiver for communicating information to and/or receiving information from an external device, or the like. In some embodiments, electrical circuitry 312 may be used for processing information obtained from sensor 206, and transmitting information to one or more external devices used by patients and/or healthcare providers to, among other things, track the patient's blood glucose level over time.

As shown in FIG. 3B, when sensor unit 102 is positioned within sensor unit receiving area 104, conductive member 212 contacts substrate 310. For example, conductive member 212 may make electrical contact to one or more electrical contacts (not shown) present on substrate 310 that are (electrically) coupled to, or which may be configured to couple to (e.g., via a switch or other similar mechanism (not shown)), electronic circuitry 312. Conductive member 212 thereby allows sensor 206 to be in electrical contact with electronics (e.g., electrical circuitry 312). In some embodiments, conductive member 212 may define multiple, separate electrical paths between sensor 206 and substrate 310 (and thus electronic circuitry 312). For example, only predefined portions of conductive member 212 may be electrically conductive (e.g., one or more vertical contacts that extend between sensor 206 and substrate 310).

Sensor unit 102 may be secured within sensor unit receiving area 104 using any suitable mechanism (e.g., friction, adhesives, etc.).

As described, sensor unit 102 may include a sealed, separately sterilized region 226 including at least a portion of sensor 206 and introducer 214. Sensor unit 102 may be positioned within sensor unit receiving area 104 of the sensor carrier 106 and electronics 312 may be positioned within electronics receiving area 300 of sensor carrier 106 so as to form sensor assembly 100 having sensor 206 electrically connected to electronics 312 while maintaining sterilization of the sterilized region 226 of sensor unit 102.

Figure 4A:
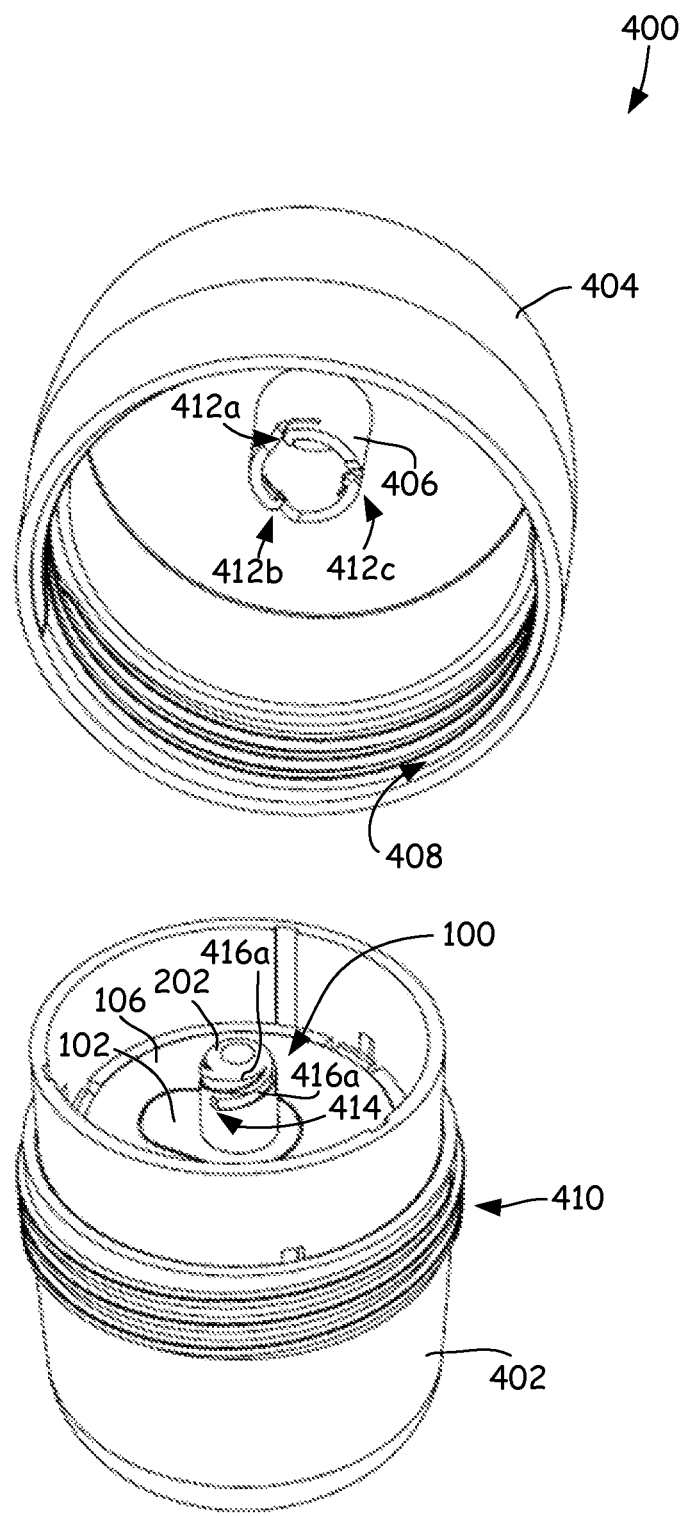
FIG. 4A is an exploded, perspective view of an insertion device for a sensor assembly provided in accordance with one or more embodiments.

FIG. 4A is an exploded, perspective view of an insertion device 400 for sensor assembly 100 provided in accordance with one or more embodiments. With reference to FIG. 4A, in some embodiments, insertion device 400 includes an insertion unit 402 having sensor assembly 100 positioned therein. For example, the interior of insertion device 400 may serve as a receiving area for the sensor assembly 100. Sensor assembly 100 includes sensor carrier 106 having sensor unit 102 coupled thereto. Insertion shaft cover 202 is also shown.

Insertion device 400 includes a removable cover 404 that has an interface unit 406 that interfaces with insertion shaft cover 202 such that removal of removable cover 404 removes insertion shaft cover 202 from sensor assembly 100 so as to expose insertion shaft 216 of introducer 214 and sensor 206 (FIG. 2B). For example, removable cover 404 may have internal threads 408 (e.g., forming a threaded cap) that engage with external threads 410 on interface unit 406. Interface unit 406, in some embodiments, may include one or more fingers 412a-c that engage with corresponding notch features on insertion shaft cover 202 (only one notch 414 is shown in FIG. 4A) so that rotation of removable cover 404 causes rotation of insertion shaft cover 202. Other configurations for removing insertion shaft cover 202 are described further below. Other numbers and/or types of fingers and/or engagement mechanisms between removable cover 404 and insertion shaft cover 202 may be used.

Figure 4B:
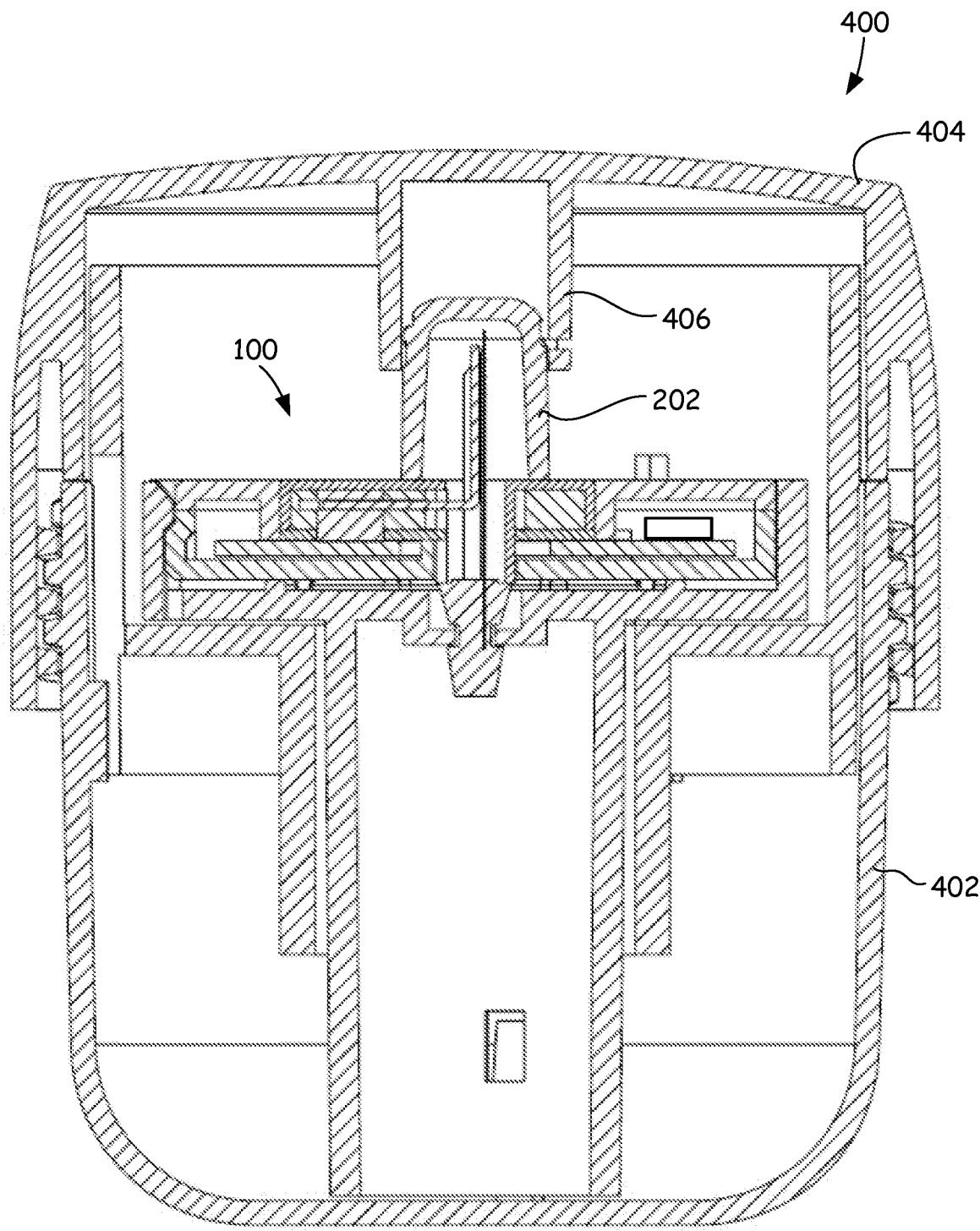
FIG. 4B is a cross-sectional view of an insertion device in which an interface unit of a removable cover is engaged with an insertion shaft cover in accordance with some embodiments.
Figure 4C:
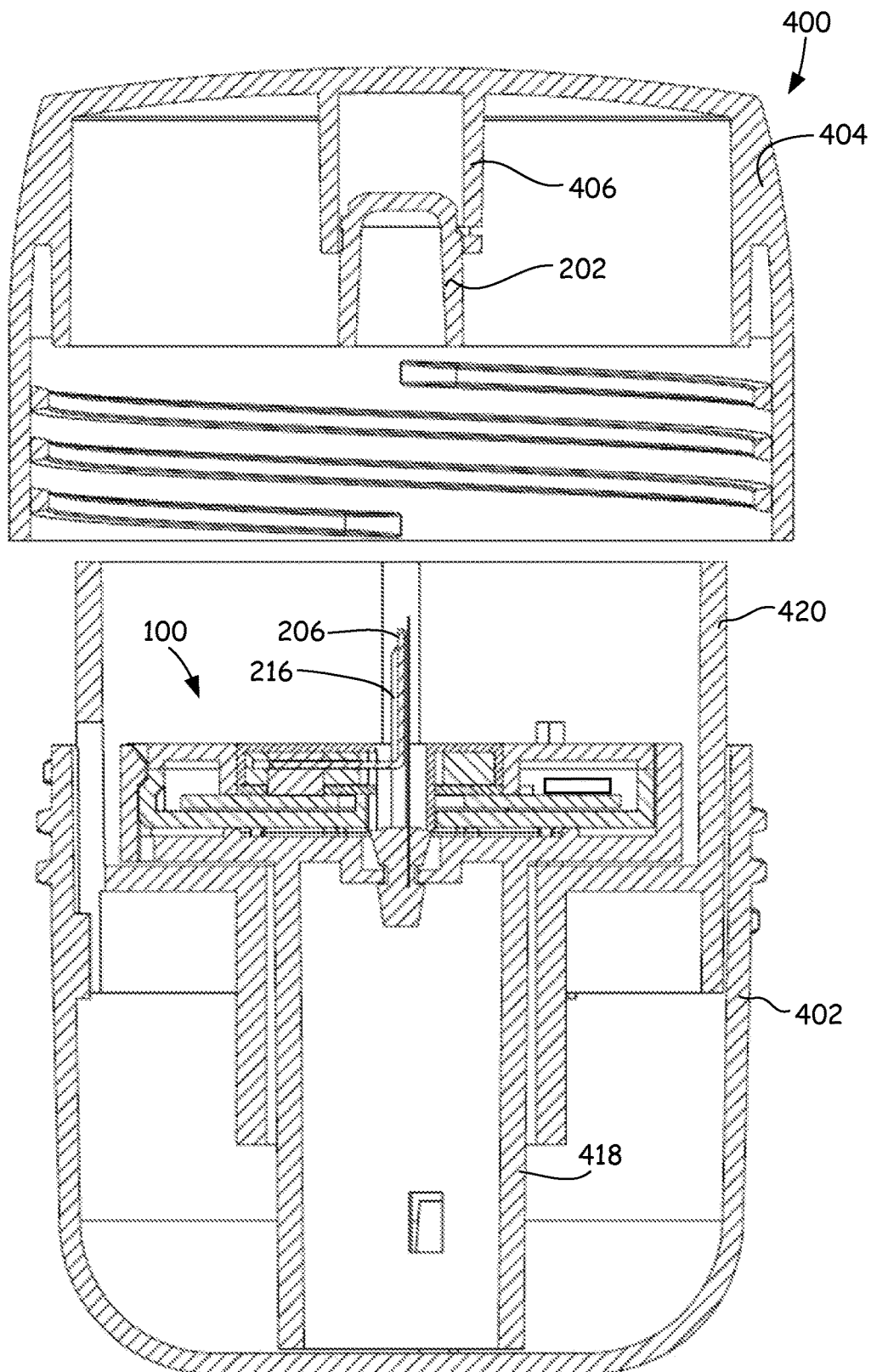
FIG. 4C is a cross-sectional view of an insertion device in which an insertion shaft cover is removed from a sensor assembly with a removable cover in accordance with some embodiments.
Figure 4D:
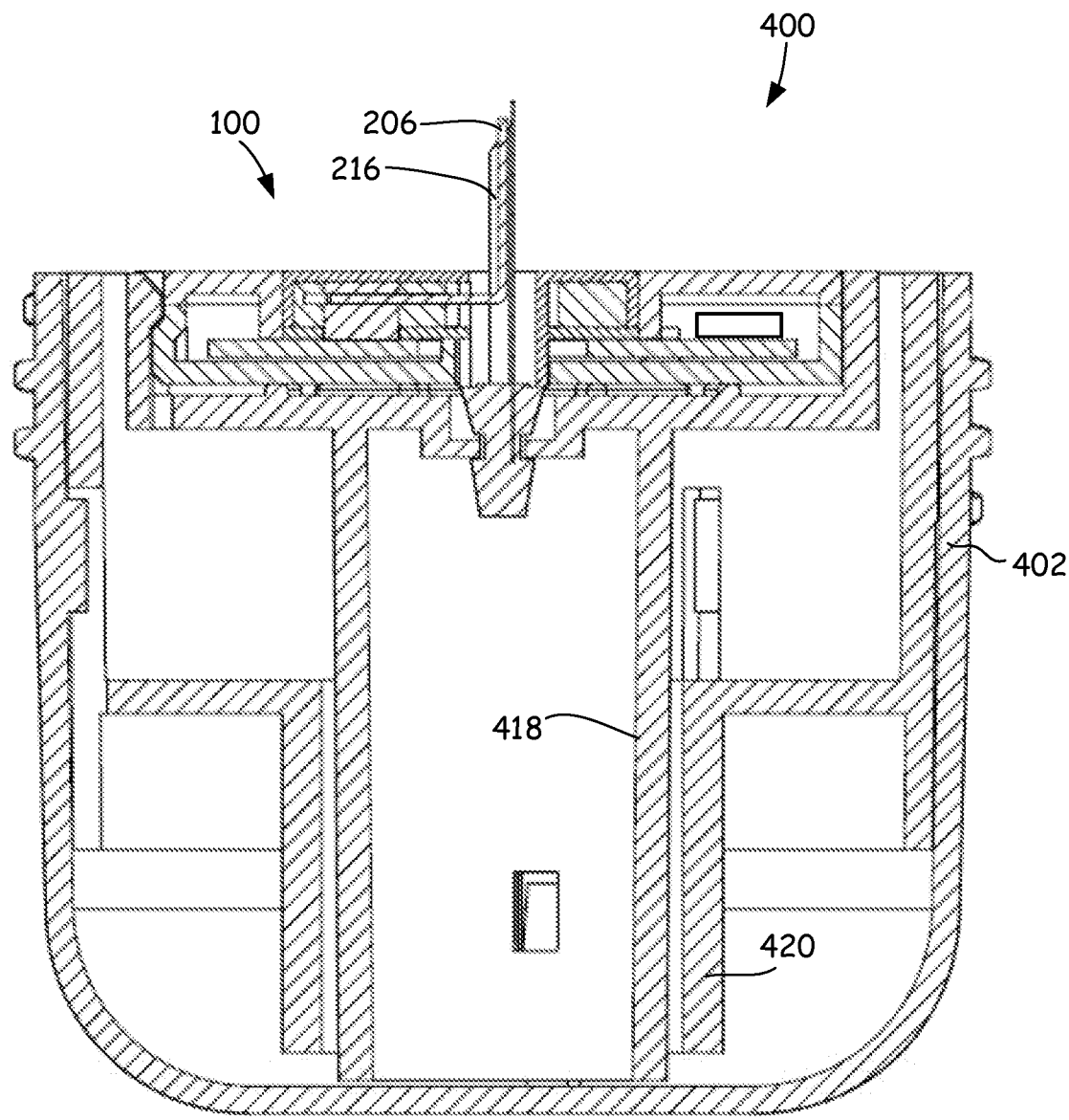
FIG. 4D illustrates a cross-sectional view of an insertion device with a sliding mechanism depressed within an insertion unit during insertion in accordance with some embodiments.

In operation, when removable cover 404 is threaded onto insertion unit 402, fingers 412a-c slide within guide channels on insertion shaft cover 202 (only two guide channels 416a-b are shown in FIG. 4A) until they engage in a respective notch 414. This causes the fingers 412a-c to lock within each notch 414. FIG. 4B is a cross-sectional view of insertion device 400 in which interface unit 406 of removable cover 404 is engaged with insertion shaft cover 202 in accordance with some embodiments. Thereafter, when removable cover 404 is unthreaded from insertion unit 402, insertion shaft cover 202 will rotate with removable cover 404 and will be removed from sensor assembly 100 when removable cover 404 is removed from insertion unit 402. FIG. 4C is a cross-sectional view of insertion device 400 in which insertion shaft cover 202 is removed from sensor assembly 100 with removable cover 404 in accordance with some embodiments. As shown in FIG. 4C, removal of removable cover 404 exposes sensor 206 and insertion shaft 216. Insertion unit 402 may then be used to insert insertion shaft 216 and sensor 206 into a patient's skin. For example, sensor assembly 100 may be supported by a supporting member 418 within insertion unit 402. A sliding member 420 may surround sensor assembly 100 (as shown in FIG. 4C) and slide relative to supporting member 418. With removable cover 404 removed, sliding member 420 may be placed on the patient and insertion unit 402 pressed toward the patient to cause insertion shaft 216 and sensor 206 to be inserted into the patient's skin. A biasing mechanism, such as a spring (not shown), may bias sliding member 420 so that it is maintained in a position around sensor assembly 100 (as shown in FIG. 4C) until insertion unit 402 is pressed for insertion. FIG. 4D illustrates a cross-sectional view of insertion device 400 with sliding member 420 depressed within insertion unit 402 during insertion in accordance with some embodiments. Other insertion device configurations may be used.

Figure 4E:
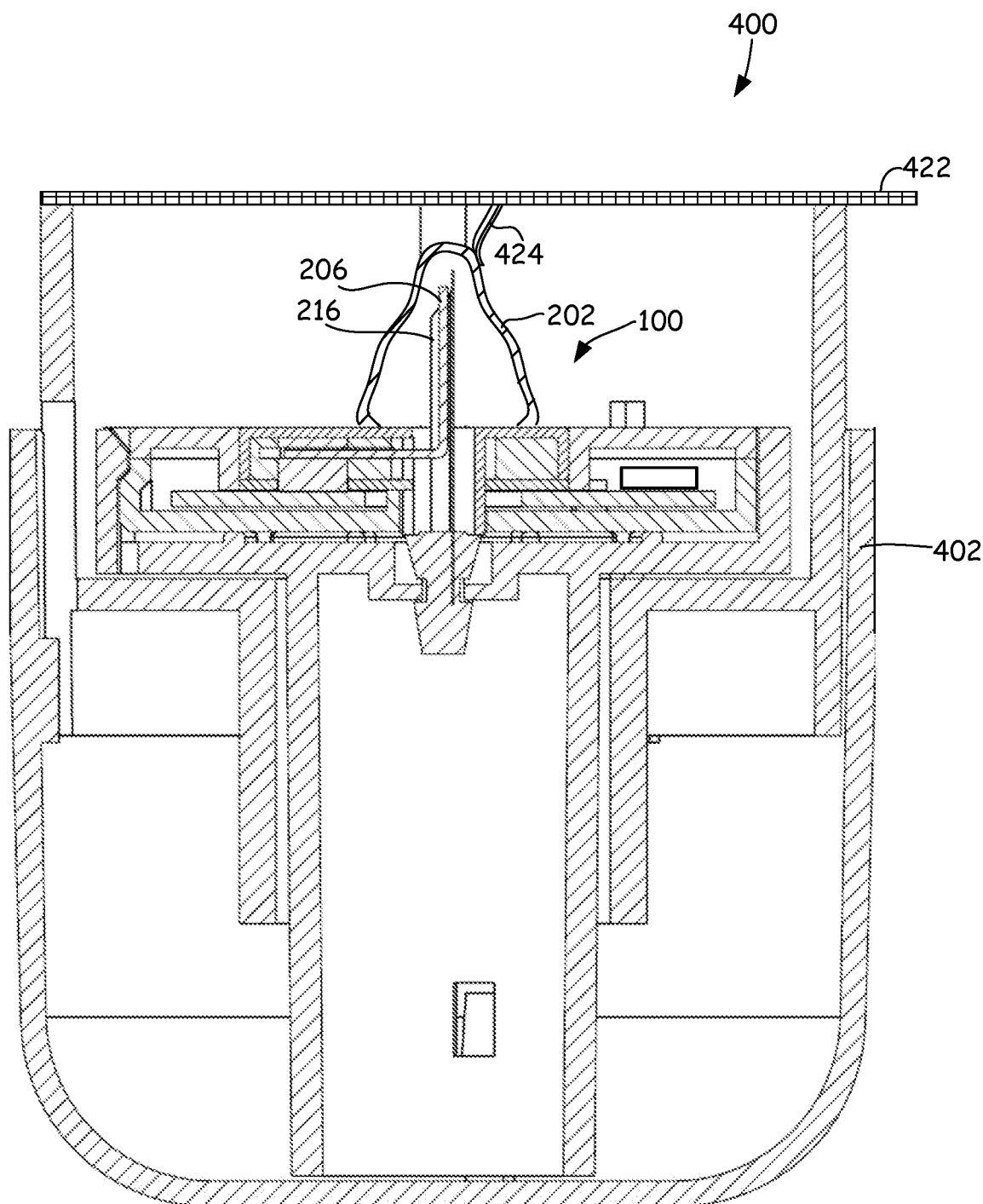
FIG. 4E illustrates a cross-sectional view of an alternative embodiment of an insertion device of FIGS. 4A-4D which employs a peelable cover in accordance with embodiments provided herein.

FIG. 4E illustrates a cross-sectional view of an alternative embodiment of insertion device 400 of FIGS. 4A-4D which employs a peelable cover in accordance with embodiments provided herein. With reference to FIG. 4E, insertion device 400 includes insertion unit 402 having a peelable cover 422 formed thereon.

Peelable cover 422 may be coupled to insertion shaft cover 202 via a strap member 424, which in turn couples to insertion shaft cover 202. In this manner, when peelable cover 422 is removed, strap member 424 pulls and detaches insertion shaft cover 202 from sensor assembly 100, exposing insertion shaft 216 and sensor 206 for insertion (as previously described).

Peelable cover 422 and/or strap member 424 may be formed from plastic, polyethylene, high density polyethylene, Tyvek® available from E.I. du Pont de Nemours and Company of Wilmington, Del. or a similar material, for example. Other peelable cover and/or strap member materials may be used.

In some embodiments, such as that shown in FIG. 4E, insertion shaft cover 202 may be formed from a soft and/or flexible material (e.g., a plastic bag, polyethylene, high density polyethylene, Tyvek® available from E.I. du Pont de Nemours and Company of Wilmington, Del., or the like). A soft and/or flexible insertion shaft cover 202 may be used with the other embodiments described herein.

Figure 5:
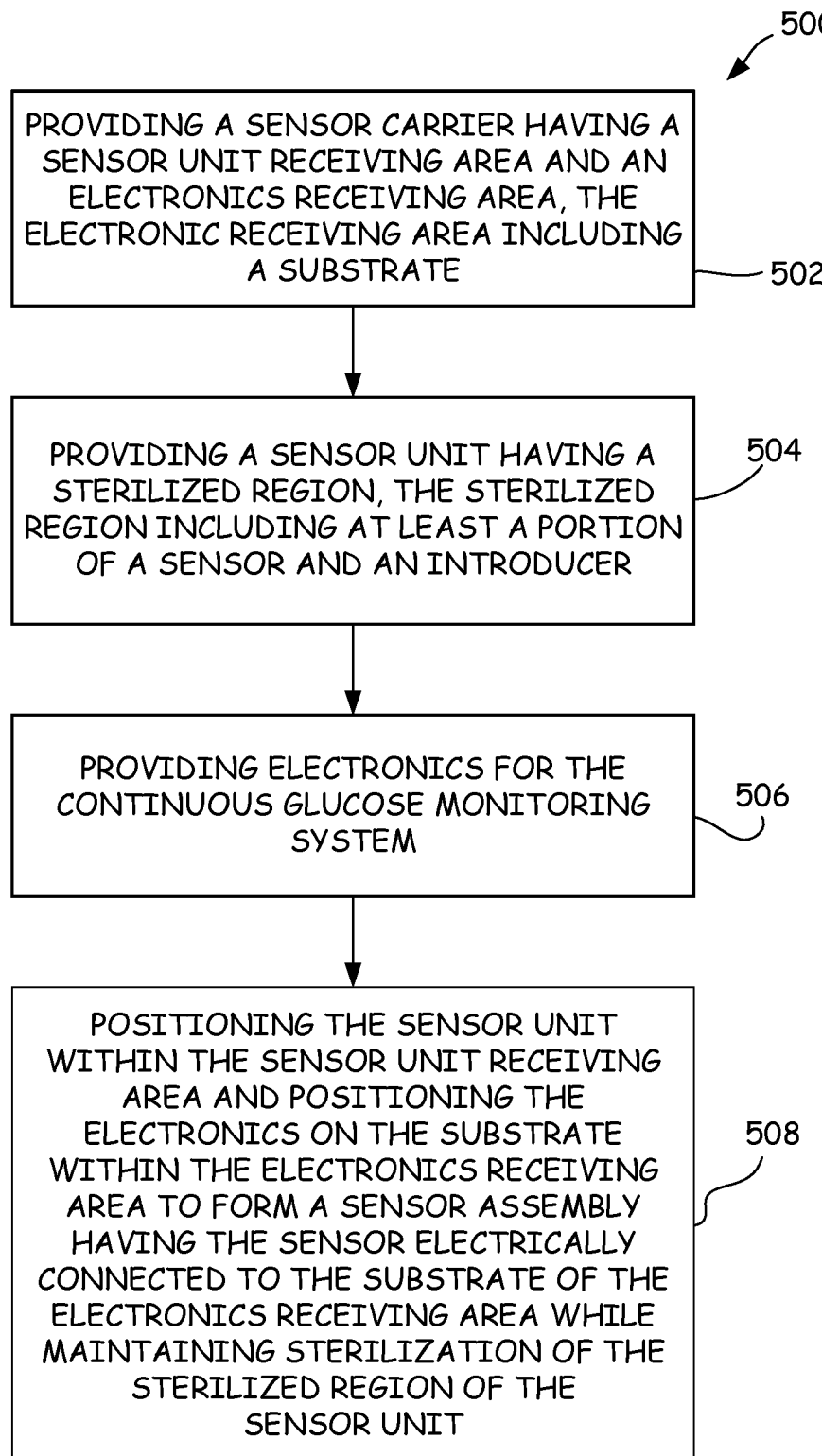
FIG. 5 is a flowchart of an example method of forming a sensor assembly for a continuous glucose monitoring system in accordance with embodiments provided herein.

FIG. 5 is a flowchart of an example method 500 of forming a sensor assembly for a continuous glucose monitoring system in accordance with embodiments provided herein. Method 500 includes providing a sensor carrier having a sensor unit receiving area and an electronics receiving area, the electronics receiving area including a substrate (Block 502); providing a sensor unit having a sterilized region, the sterilized region including at least a portion of a sensor and an introducer (Block 504); providing electronics for the continuous glucose monitoring system (Block 506); and positioning the sensor unit within the sensor unit receiving area of the sensor carrier and positioning the electronics on the substrate within the electronics receiving area of the sensor carrier so as to form a sensor assembly having the sensor electrically connected to the substrate of the electronics receiving area while maintaining sterilization of the sterilized region of the sensor unit (Block 508).

Figure 6:
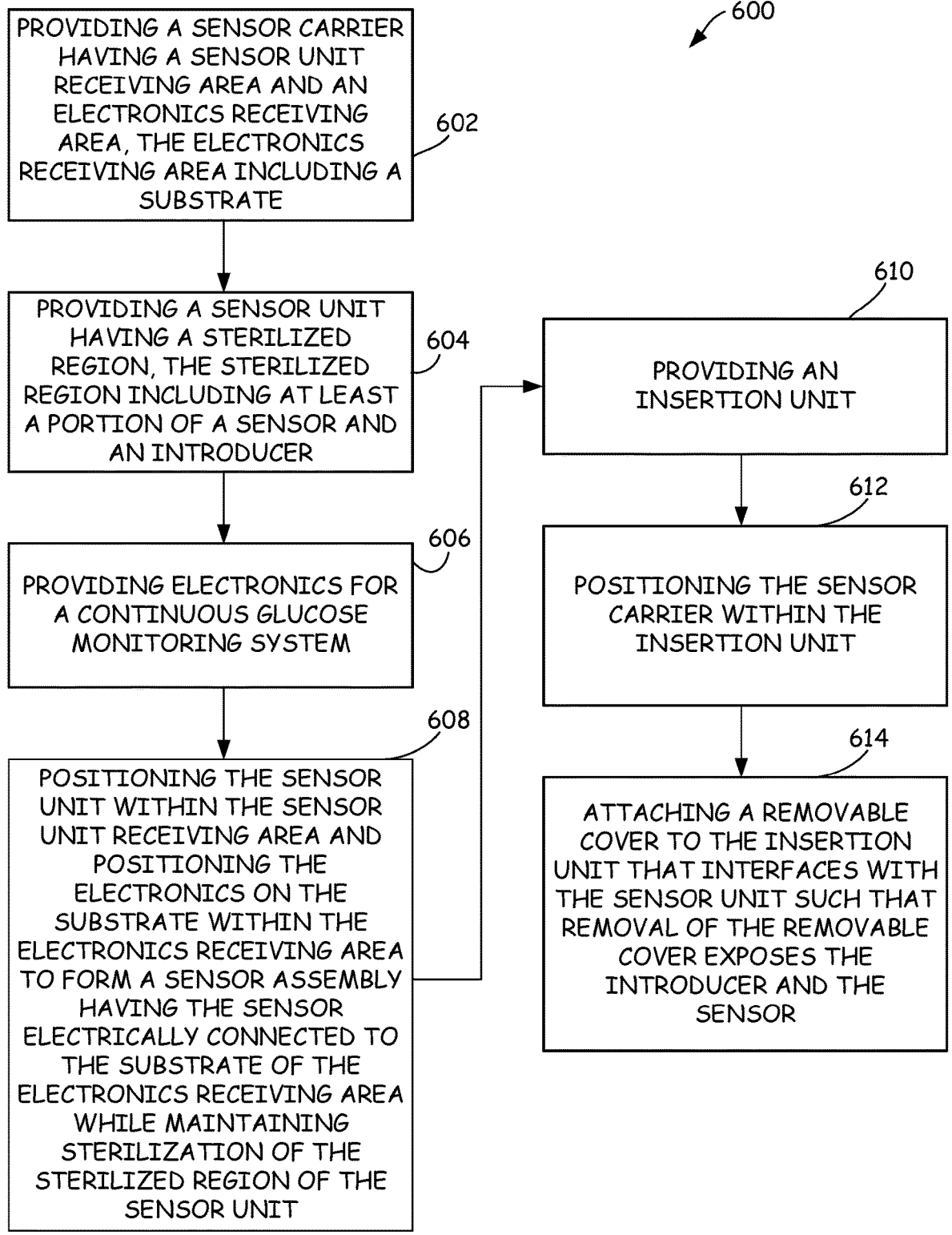
FIG. 6 is a flowchart of an example method of forming an insertion device for a continuous glucose monitoring system in accordance with embodiments provided herein.

FIG. 6 is a flowchart of an example method 600 of forming an insertion device for a continuous glucose monitoring system in accordance with embodiments provided herein. Method 600 includes providing a sensor carrier having a sensor unit receiving area and an electronics receiving area, the electronics receiving area including a substrate (Block 602); providing a sensor unit having a sterilized region, the sterilized region including at least a portion of a sensor and an introducer (Block 604); providing electronics for the continuous glucose monitoring system (Block 606); positioning the sensor unit within the sensor unit receiving area of the sensor carrier and positioning the electronics on the substrate within the electronics receiving area of the sensor carrier so as to form a sensor assembly having the sensor electrically connected to the substrate of the electronics receiving area while maintaining sterilization of the sterilized region of the sensor unit (Block 608); providing an insertion unit (Block 610); positioning the sensor carrier within the insertion unit (Block 612); and attaching a removable cover to the insertion unit that interfaces with the sensor unit such that removal of the removable cover exposes the introducer and the sensor (Block 614).

Figure 7:
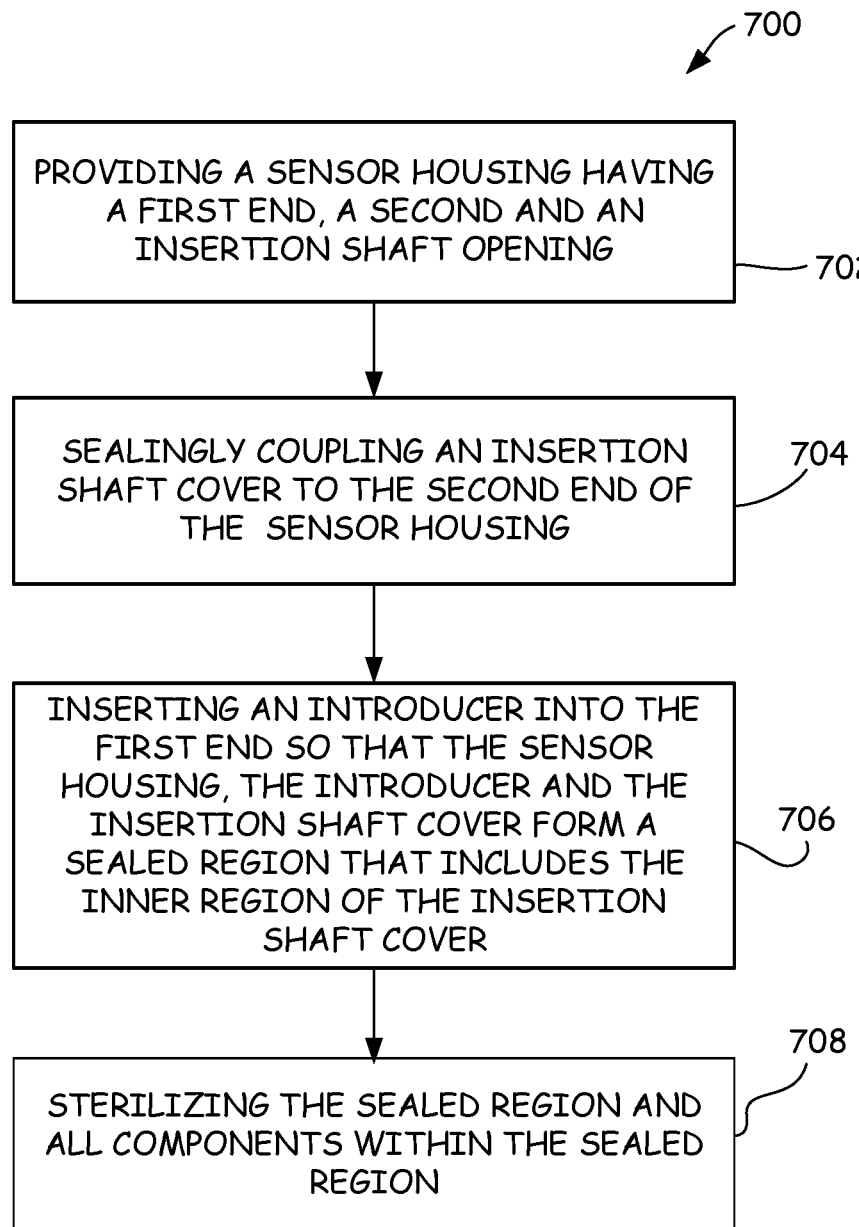
FIG. 7 is a flowchart of an example method of forming a sensor unit for a continuous glucose monitoring system in accordance with embodiments provided herein.

FIG. 7 is a flowchart of an example method 700 of forming a sensor unit for a continuous glucose monitoring system in accordance with embodiments provided herein. Method 700 includes providing a sensor housing having a first end, a second and an insertion shaft opening (Block 702). For example, the sensor unit may have a first end configured to receive an insertion shaft of an introducer, a second end having a sealing surface configured to seal against an insertion shaft cover, and an insertion shaft opening that extends between the first end and the second end and having a width that allows an insertion shaft of the introducer to travel through the opening. A portion of the sensor and insertion shaft of the introducer may be positioned within the insertion shaft opening of the sensor unit. Method 700 also includes sealingly coupling an insertion shaft cover to the second end of the sensor housing (Block 704); inserting an introducer into the first end of the sensor housing so that the sensor housing, the introducer and the insertion shaft cover form a sealed region that includes the inner region of the insertion shaft cover (Block 706); and sterilizing the sealed region and all components within the sealed region (Block 708). For example, electron or gamma beam sterilization of the sealed region may be performed.

While described primarily with regard to continuous glucose monitoring, it will be understood that the separately sterilizable regions described herein, such as within the sensor units and/or sensor assemblies of FIGS. 1A-7, may be employed in other monitoring applications to monitor other body fluid levels such as cholesterol, Hb1AC, ketones, PH, oxygen saturation, etc.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a smartphone," does not imply that any or all of the three items of that list are mutually exclusive and does not imply that any or all of the three items of that list are comprehensive of any category.

A description of an embodiment with several components or features does not imply that all or even any of such components and/or features are required. On the contrary, a variety of optional components are described to illustrate the wide variety of possible embodiments in accordance with this disclosure. Unless otherwise specified explicitly, no component and/or feature is essential or required.

When an ordinal number (such as "first," "second," "third," and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget." Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

The foregoing description discloses only example embodiments. Modifications of the above-disclosed apparatus and methods which fall within the scope of this disclosure will be readily apparent to those of ordinary skill in the art.

What is claimed is:

1. A sensor assembly for a continuous glucose monitoring system, comprising:
    a sensor carrier having a sensor unit receiving area and an electronics receiving area, the electronics receiving area including a substrate;

a sensor unit, comprising:
    a sensor housing, a conductive member, a sensor comprising an insertion portion and a contact portion, an insertion shaft cover, an introducer comprising a handle and an insertion shaft, and a sealed, sterilized region,
    wherein the sensor housing comprises:
        a first opening extending from a bottom surface of the sensor housing, and
        a second opening laterally displaced from the first opening and extending from the bottom surface to a top surface of the sensor housing,
    wherein the insertion shaft cover is sealed against the top surface of the sensor housing and the handle is sealed against the bottom surface of the sensor housing,
    wherein the sealed, sterilized region extends from an inner surface of the insertion shaft cover, through the second opening, and to the handle of the introducer,
    wherein the insertion portion of the sensor and the insertion shaft are within the sealed, sterilized region,
    wherein the conductive member is positioned outside of the sealed, sterilized region and is in electrical contact with the contact portion of the sensor outside of the sealed, sterilized region, and
    wherein the conductive member extends through the first opening of the sensor housing; and
electronics for the continuous glucose monitoring system;
wherein the sensor unit is positioned within the sensor unit receiving area of the sensor carrier and the electronics are positioned on the substrate within the electronics receiving area of the sensor carrier so as to form the sensor assembly having the sensor electrically connected to the substrate of the electronics receiving area via the conductive member while maintaining sterilization of the sealed, sterilized region of the sensor unit.

2. An insertion device, comprising:
a receiving area housing the sensor assembly of claim 1; and
a cover that covers the receiving area and the sensor assembly, wherein the cover is configured so that removal of the cover exposes the introducer and allows the insertion device to insert the introducer and the sensor into a patient for continuous glucose monitoring.

3. The insertion device of claim 2, wherein the cover includes a threaded cap coupled to the sensor unit, the threaded cap configured so that when the threaded cap is unthreaded from the receiving area, the introducer is exposed to allow the insertion device to insert the introducer and the sensor into the patient for continuous glucose monitoring.

4. The sensor assembly of claim 1, wherein the sensor housing further comprises:
a top member comprising the top surface;
a bottom member comprising the bottom surface; and
a spacer pad disposed between the top member and the bottom member,
wherein the spacer pad comprises a first opening and a second opening corresponding to the first opening and the second opening of the sensor housing.

5. The sensor assembly of claim 4,
wherein the top member comprises a cylindrical member extending from the top surface thereof, and
wherein the cylindrical member extends from the top surface of the top member, through the second opening, and to the bottom surface of the bottom member.

6. The sensor assembly of claim 4, wherein the first opening extends from the bottom member to a top surface of the spacer pad.

7. An insertion device for a continuous glucose monitoring system, comprising:
an insertion unit;
a sensor carrier positioned within the insertion unit and having a sensor unit receiving area and an electronics receiving area, the electronics receiving area including a substrate;
a sensor unit, comprising:
    a sensor housing, a conductive member, a sensor comprising an insertion portion and a contact portion, an insertion shaft cover, an introducer comprising a handle and an insertion shaft, and a sealed, sterilized region,
    wherein the sensor housing comprises:
        a first opening extending from a bottom surface of the sensor housing, and
        a second opening laterally displaced from the first opening and extending from the bottom surface to a top surface of the sensor housing,
    wherein the insertion shaft cover is sealed against the top surface of the sensor housing and the handle is sealed against the bottom surface of the sensor housing,
    wherein the sealed, sterilized region extends from an inner surface of the insertion shaft cover, through the second opening, and to the handle of the introducer,
    wherein the insertion portion of the sensor and the insertion shaft are within the sealed, sterilized region,
    wherein the conductive member is positioned outside of the sealed, sterilized region and is in electrical contact with the contact portion of the sensor outside of the sealed, sterilized region, and
    wherein the conductive member extends through the first opening of the sensor housing; and
electronics for the continuous glucose monitoring system;
wherein the sensor unit is positioned within the sensor unit receiving area of the sensor carrier and the electronics are positioned on the substrate within the electronics receiving area of the sensor carrier so as to form the sensor unit having the sensor electrically connected to the substrate of the electronics receiving area via the conductive member while maintaining sterilization of the sealed, sterilized region of the sensor unit; and
a removable cover attached to the insertion unit that interfaces with the sensor unit such that removal of the removable cover exposes the introducer and the insertion portion of the sensor.

8. The insertion device of claim 7, wherein the sensor housing further comprises:
a top member comprising the top surface;
a bottom member comprising the bottom surface; and
a spacer pad disposed between the top member and the bottom member
wherein the spacer pad comprises a first opening and a second opening corresponding to the first opening and the second opening of the sensor housing.

9. The insertion device of claim 8,
wherein the top member comprises a cylindrical member extending from the top surface, and
wherein the cylindrical member extends from the top surface of the top member, through the second opening, and to the bottom surface of the bottom member.

10. The insertion device of claim 9,
wherein the sensor carrier comprises a top carrier member coupled to a bottom carrier member, and wherein the bottom carrier member comprises an opening configured to receive the cylindrical member.

11. The insertion device of claim 9,
wherein the spacer pad comprises a first opening and a second opening,
wherein the conductive member extends through the first opening,
wherein the contact portion of the sensor is in contact with the conductive member and is disposed between the spacer pad and the top member of the sensor housing, and
wherein the insertion portion of the sensor and the insertion shaft extend through the second opening.

12. The insertion device of claim 7,
wherein the removable cover is a peelable cover,
wherein the peelable cover is coupled to the insertion shaft cover via a strap member, and
wherein, when the peelable cover is peeled, the strap member pulls the insertion shaft cover off from the sensor unit, thereby exposing the insertion shaft and the insertion portion of the sensor for insertion into a patient.

13. A method of forming a sensor assembly for a continuous glucose monitoring system, comprising:
providing a sensor carrier having a sensor unit receiving area and an electronics receiving area, the electronics receiving area including a substrate;
providing electronics for the continuous glucose monitoring system;
providing a sensor unit having a sensor housing, a conductive member, a sensor, an insertion shaft cover, an introducer comprising a handle and an insertion shaft, and a sealed, sterilized region within the sensor unit,
wherein the sensor housing comprises:
a first opening extending from a bottom surface of the sensor housing, and
a second opening laterally displaced from the first opening and extending from the bottom surface to a top surface of the sensor housing,
wherein the insertion shaft cover is sealed against the top surface of the sensor housing and the handle is sealed against the bottom surface of the sensor housing,
wherein the sealed, sterilized region extends from an inner surface of the insertion shaft cover, through the second opening, and to the handle of the introducer,
wherein an insertion portion of the sensor and the insertion shaft are within the sealed, sterilized region,
wherein the conductive member is positioned outside of the sealed, sterilized region and is in electrical contact with the sensor outside of the sealed, sterilized region,
wherein the conductive member extends through the first opening of the sensor housing; and
positioning the sensor unit within the sensor unit receiving area of the sensor carrier and positioning the electronics on the substrate within the electronics receiving area of the sensor carrier so as to form the sensor assembly having the sensor electrically connected to the substrate of the electronics receiving area via the conductive member while maintaining sterilization of the sealed, sterilized region of the sensor unit.

14. A method of forming an insertion device for a continuous glucose monitoring system, comprising:
providing a sensor carrier having a sensor unit receiving area and an electronics receiving area, the electronics receiving area including a substrate;
providing electronics for the continuous glucose monitoring system;
providing a sensor unit having a sensor housing, a conductive member, a sensor comprising an insertion portion and a contact portion, an insertion shaft cover, an introducer comprising a handle and an insertion shaft, and a sealed, sterilized region within the sensor unit,
wherein the sensor housing comprises:
a first opening extending from a bottom surface of the sensor housing, and
a second opening laterally displaced from the first opening and extending from the bottom surface to a top surface of the sensor housing,
wherein the insertion shaft cover is sealed against the top surface of the sensor housing and the handle is sealed against the bottom surface of the sensor housing,
wherein the sealed, sterilized region extends from an inner surface of the insertion shaft cover, through the second opening, and to the handle of the introducer,
wherein the insertion portion of the sensor and the insertion shaft are within the sealed, sterilized region,
wherein the conductive member is positioned outside of the sealed, sterilized region and is in electrical contact with the contact portion of the sensor outside of the sealed, sterilized region, and
wherein the conductive member extends through the first opening of the sensor housing; and
positioning the sensor unit within the sensor unit receiving area of the sensor carrier and positioning the electronics on the substrate within the electronics receiving area of the sensor carrier so as to form a sensor assembly having the sensor electrically connected to the substrate of the electronics receiving area via the conductive member while maintaining sterilization of the sealed, sterilized region of the sensor unit;
providing an insertion unit;
positioning the sensor carrier within the insertion unit; and
attaching a removable cover to the insertion unit that interfaces with the sensor unit such that removal of the removable cover exposes the insertion shaft and the sensor.

15. The method of claim 14 wherein the removable cover comprises a threaded cap.

16. The method of claim 14,
wherein the second opening comprises a width that allows the insertion shaft of the introducer to travel through the second opening, and
wherein the bottom surface of the sensor housing is configured to receive the insertion shaft.

17. A method of forming a sterilized sensor unit for a continuous glucose monitor comprising:
providing a sensor, a conductive member, an introducer having an insertion shaft and a handle, and an insertion shaft cover;
providing a sensor housing having:
a first end configured to receive the insertion shaft of the introducer;
a second end having a sealing surface configured to seal against the insertion shaft cover, the second end opposite the first end;
a first opening through which the conductive member extends;
a second opening that extends between the first end and the second end and having a width that allows the insertion shaft of the introducer to travel through the second opening; and a sealed, sterilized region extending from an inner surface of the insertion shaft cover, through the second opening, and to the handle of the introducer, wherein an insertion portion of the sensor and the insertion shaft of the introducer extend through the second opening of the sensor housing and are within the sealed, sterilized region, wherein the second opening is laterally displaced from the first opening;

sealingly coupling the insertion shaft cover to the second end of the sensor housing, inserting the introducer into the first end, wherein the handle of the introducer is sealingly coupled to the first end of the sensor housing;

sterilizing the sealed, sterilized region and the insertion portion of the sensor and the insertion shaft within the sealed, sterilized region separately from any other component, wherein the conductive member is positioned outside of the sealed, sterilized region and is in electrical contact with a contact portion of the sensor outside of the sealed, sterilized region.

18. A sterilized sensor unit for a continuous glucose monitor, comprising:

a sensor, a conductive member, an introducer having an insertion shaft and a handle, and an insertion shaft cover; and a sensor housing having:

a top member, a bottom member, and a spacer pad disposed between the top member and the bottom member, a first opening extending through the bottom member and the spacer pad, wherein the conductive member extends through the first opening; and a second opening extending through the bottom member, the spacer pad, and the top member and having a width that allows the insertion shaft of the introducer to travel through the second opening; and a sealed, sterilized region extending from an inner surface of the insertion shaft cover, through the second opening, and to the handle of the introducer, wherein an insertion portion of the sensor and a portion of the insertion shaft of the introducer extend through the second opening of the sensor housing and are within the sealed, sterilized region;

wherein the handle is sealingly coupled to an outer surface of the bottom member, wherein the insertion shaft cover is sealingly coupled to an outer surface of the top member, and wherein the conductive member is positioned outside of the sealed, sterilized region and is in electrical contact with a contact portion of the sensor outside of the sealed, sterilized region.

19. The sterilized sensor unit of claim 18, wherein the sterilized sensor unit is configured to be housed within an insertion unit, and wherein the insertion unit comprises a peelable cover providing access to the sterilized sensor unit.

20. The sterilized sensor unit of claim 19, wherein the peelable cover is coupled to the insertion shaft cover via a strap member, and wherein, when the peelable cover is peeled, the strap member pulls the insertion shaft cover off from the sterilized sensor unit, thereby exposing the insertion shaft and the insertion portion of the sensor for insertion into a patient.

* * * * *